United States Patent
Popp et al.

(10) Patent No.: US 6,887,700 B2
(45) Date of Patent: May 3, 2005

(54) PROCESS FOR THE ENZYMATIC PREPARATION OF ENANTIOPURE 1, 3-DIOXOLAN-4-ONE AND 1,3-OXATHIOLAN-5-ONE DERIVATIVES

(75) Inventors: Alfred Popp, Unterhaching (DE); Jürgen Stohrer, Pullach (DE); Hermann Petersen, Burghausen (DE); Andrea Gilch, Mauern (DE); Jodoca Rockinger-Mechlem, Gilching (DE)

(73) Assignee: Consortium für Elektrochemische Industrie GmbH, München (DE)

( * ) Notice: Subject to any disclaimer, the term of this patent is extended or adjusted under 35 U.S.C. 154(b) by 210 days.

(21) Appl. No.: 10/059,774

(22) Filed: Jan. 30, 2002

(65) Prior Publication Data
US 2003/0143698 A1 Jul. 31, 2003

(30) Foreign Application Priority Data
Jan. 31, 2001 (DE) .......................................... 101 04 231

(51) Int. Cl.$^7$ ................................................. C12P 17/16
(52) U.S. Cl. ....................... 435/280; 549/453; 549/341; 549/354; 435/118
(58) Field of Search ................................ 435/280, 118; 549/453, 341, 454

(56) References Cited

FOREIGN PATENT DOCUMENTS

| WO | 9111186 | 8/1991 |
| WO | 9214743 | 9/1992 |
| WO | 00 22 157 | 4/2000 |

OTHER PUBLICATIONS

J. Wilson et al., Bioorg. Med. Chem. Lett. 1993, 3(2), pp. 169–174.

J. Org. Chem. 1992, 57(21), pp. 5563–5565.

Chen, C.-S. et al., J. Am. Ehem. Soc. 104, pp. 7294–7299.

Patent Abstracts of Japan JP 07075594A.

Patent Abstracts of Japan JP 08023997.

Bull. Chem. Soc. Jpn. 69, pp. 2977–2987 (1996).

Hof R. P. et al., (May 7, 1996) Journal of Organic Chemistry, American Chemical Society, Easton, US, vol. 61, No. 10, pp. 3423–3427.

*Primary Examiner*—Irene Marx
(74) *Attorney, Agent, or Firm*—Collard & Roe, P.C.

(57) ABSTRACT

A process is provided for preparing an enantiopure 1,3-dioxolan-4-one or 1,3-oxathiolan-5-one derivative, which includes bringing a mixture containing enantiomeric 1,3-dioxolan-4-one or 1,3-oxathiolan-5-one derivatives and an enzyme with hydrolytic activity into contact in the presence of a nucleophile. Cleaving a dioxolanone/oxathiolanone ring of one enantiomer occurs by the enzyme with hydrolytic activity and, after the cleavage of one enantiomer has taken place, the uncleaved enantiomer of the 1,3-dioxolan-4-one or 1,3-oxathiolan-5-one derivative is isolated.

14 Claims, No Drawings

PROCESS FOR THE ENZYMATIC PREPARATION OF ENANTIOPURE 1,3-DIOXOLAN-4-ONE AND 1,3-OXATHIOLAN-5-ONE DERIVATIVES

BACKGROUND OF THE INVENTION

1. Field of the Invention

The invention relates to a process for the enzymatic preparation of enantiopure 1,3-dioxolan-4-one and 1,3-oxathiolan-5-one derivatives.

2. The Prior Art

Enantiopure derivatives are used as starting materials and intermediates in the synthesis of agrochemicals and pharmaceuticals. Many of these compounds are currently prepared and marketed as racemate or mixture of diastereomers. However, in many cases, the desired physiological effect is brought about by only one enantiomer/diastereomer. The other isomer is, in the most favorable case, inactive, but it may also counteract the desired effect or even be toxic. Processes for separating racemates are therefore of increasing importance for the preparation of compounds of high enantiopurity.

It is known that racemates of chiral compounds can be separated with the aid of enzymes. A large number of publications describe enzymatic kinetic resolutions of racemates of esters with lipases and esterases. However, to date, there is no process which permits the simple separation of 1,3-dioxolan-4-one and 1,3-oxathiolan-5-one derivatives. Enantiopure 1,3-dioxolan-4-ones are of great interest for the preparation of compounds with antiviral activity, such as, for example, the 1,3-dioxolanyl-nucleoside "dioxane-T" (NB=thymine in equation 1) and similar structures (*Bioorg. Med. Chem. Lett.* 1993, 3(2), pp. 169–174).

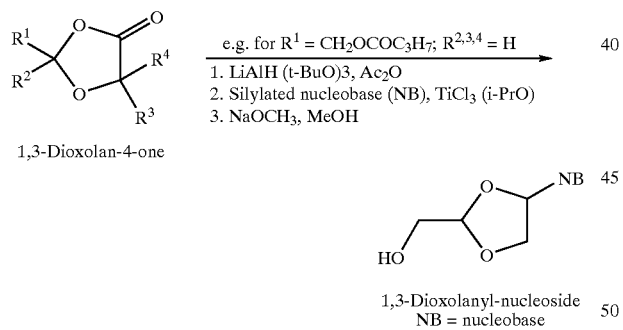

1,3-Dioxolan-4-one e.g. for $R^1 = CH_2OCOC_3H_7$; $R^{2,3,4} = H$
1. LiAlH (t-BuO)3, Ac$_2$O
2. Silylated nucleobase (NB), TiCl$_3$ (i-PrO)
3. NaOCH$_3$, MeOH 1,3-Dioxolanyl-nucleoside
NB = nucleobase Equation 1

For preparing enantiopure 1,3-dioxolanyl-nucleosides, the separation into the enantiomers has to date been carried out at the considerably more costly nucleoside stage. This process was described for the first time by L. J. Wilson et al. (*Bioorg. Med. Chem. Lett.* 1993, 3(2), pp. 169–174). The butyric ester of the primary hydroxyl group of a 1,3-dioxolanyl-nucleoside is in this case hydrolyzed with the aid of pig liver esterase, and the two pure enantiomers are thus obtained in good optical yields. WO 00/22157 (inventors: Yao, Y. et al.) describes a variant of this process by resolution in nonhomogeneous systems.

Enantiopure 1,3-oxathiolan-5-ones are likewise of great interest for the preparation of compounds with antiviral activity, such as, for example, the 1,3-oxathiolanyl-nucleoside Coviracil® (also Emtricitabine, formerly FTC, 4-amino-5-fluoro-1-[(2R, 5S)-2-(hydroxymethyl)-1,3-oxathiolan-5-yl]-2(1H)-pyrimidinone; equation 2) and similar structures (*J. Org. Chem.* 1992, 57(21), pp. 5563–5565, WO 91/11186, WO 92/14743, WO 00/22157).

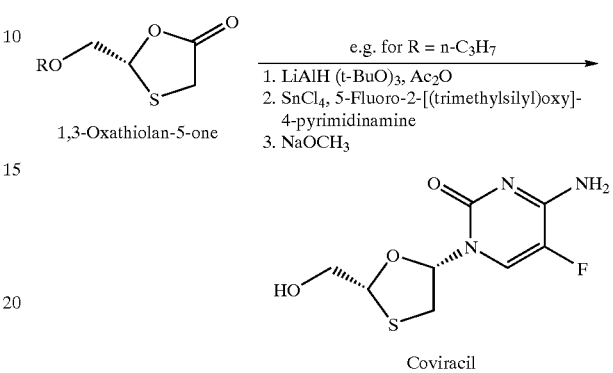

1,3-Oxathiolan-5-one e.g. for R = n-C$_3$H$_7$
1. LiAlH (t-BuO)$_3$, Ac$_2$O
2. SnCl$_4$, 5-Fluoro-2-[(trimethylsilyl)oxy]-4-pyrimidinamine
3. NaOCH$_3$ Coviracil Equation 2

For preparing enantiopure 1,3-oxathiolanyl-nucleosides it is possible for the separation into the enantiomers to take place at various stages. Thus, an enzymatic racemate resolution is possible at the oxathiolanone stage. This is described by Liotta et al. (WO 91/11186). In this case, the stereoselection is achieved by enzymatic cleavage of an ester substituent in position 2 of the oxathiolane ring (equation 3).

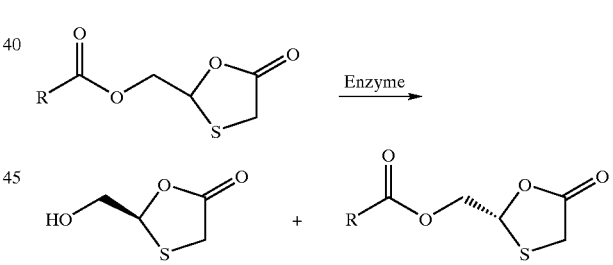

Equation 3

An example which is mentioned is the hydrolysis of the butyric ester (R=C$_3$H$_7$) in the presence of pig liver esterase (PLE).

The second possibility is racemate resolution at the considerably more costly nucleoside stage. This process is described by Liotta et al. (*J. Org. Chem.* 1992, 57(21), pp. 5563–5565 and WO 92/14743). In this case, various ester acyl groups of the nucleoside racemate are stereoselectively eliminated in the presence of lipases or proteases (equation 4).

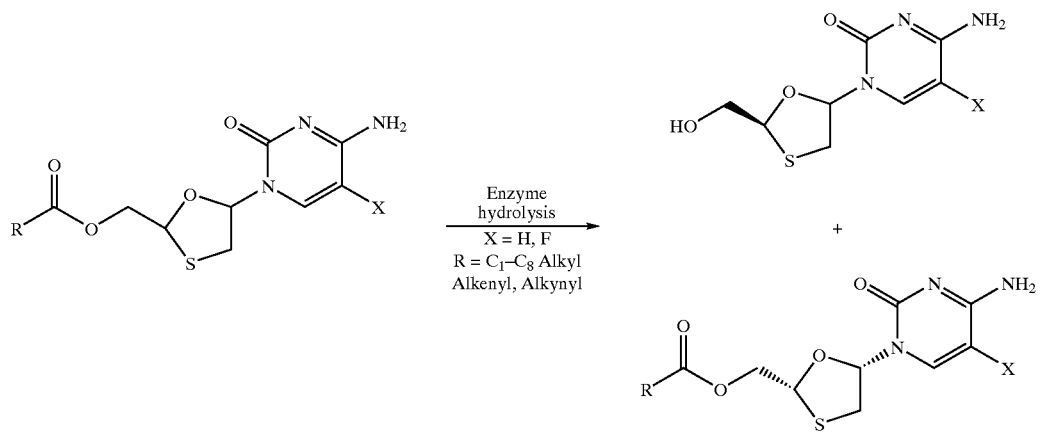

Equation 4

In some cases, high enantiomeric excesses (ee(ester) >98%) are achieved with good yields (y(ester)–45%).

An improvement of the process of WO 92/14743 is to be found in WO 00/22157 (inventors: Yao, Y. et al.) through the use of non-homogeneous reaction systems (addition of water-immiscible cosolvents) for resolution of racemates of oxathiolanyl-nucleosides.

These processes of racemate resolution at a very late stage entail the serious disadvantage of unnecessary use of materials and long plant usage, because the maximum yield of a racemate resolution is 50%. The remaining 50% (the compound with the wrong handedness) is usually discarded.

SUMMARY OF THE INVENTION

It is an object of the present invention to provide a process for preparing enantiopure 1,3-dioxolan-4-one and 1,3-oxathiolan-5-one derivatives which is cost-effective and avoids the disadvantages mentioned.

The object is achieved by a process in which a mixture containing enantiomeric 1,3-dioxolan-4-one or 1,3-oxathiolan-5-one derivatives and an enzyme with hydrolytic activity are brought into contact in the presence of a nucleophile, whereupon the dioxolanone or oxathiolanone ring of one enantiomer is cleaved by the enzyme with hydrolytic activity and, after the cleavage of one enantiomer has taken place, the uncleaved enantiomer of the 1,3-dioxolan-4-one or 1,3-oxathiolan-5-one derivative is isolated.

The process of the invention separates a mixture of enantiomers at the dioxolanone or oxathiolanone stage and thus provides an enantiopure derivative which then makes it possible for an enantiopure 1,3-dioxolanyl- or 1,3-oxathiolanyl-nucleoside to be prepared in a manner known per se.

1,3-Dioxolan-4-ones and 1,3-oxathiolan-5-ones have in the ring a hydrolysis-labile ester linkage which can be cleaved by an enzyme-catalyzed reaction. It has been found, surprisingly, that this ester linkage in the dioxolanone or oxathiolanone ring can be cleaved by an enzyme with hydrolytic activity both with high enantioselectivity and with high regioselectivity in relation to other hydrolysis-labile groups present in the compound.

The process of the invention therefore preferably comprises bringing a mixture containing enantiomeric 1,3-dioxolan-4-one or 1,3-oxathiolan-5-one derivatives into contact with an enzyme which is able to cleave an ester linkage in the presence of a nucleophile of the general formula NuH so that one enantiomer is preferentially cleaved.

This cleavage is depicted diagrammatically in equation 5.

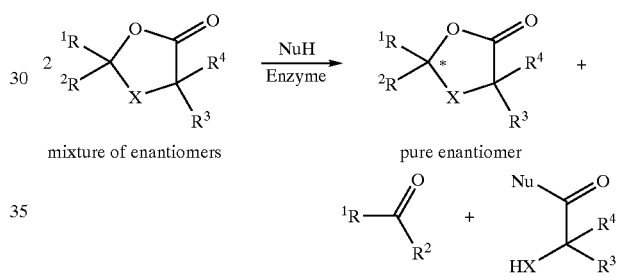

mixture of enantiomers    pure enantiomer

Equation 5 where X=oxygen or sulfur and the radicals $R^1$ and $R^2$ are different and are selected independently of one another from the group of H, substituted or unsubstituted $C_6$–$C_{18}$-aryl, $C_3$–$C_{18}$-heteroaryl, $C_1$–$C_{18}$-alkyl, $C_2$–$C_{18}$-alkenyl, $C_2$–$C_{18}$-alkynyl, $C_6$–$C_{18}$-aryl-$C_1$–$C_{18}$-alkyl, $C_3$–$C_{18}$-heteroaryl-$C_1$–$C_{18}$-alkyl, $C_6$–$C_{18}$-aryl-$C_2$–$C_{18}$-alkenyl, $C_3$–$C_{18}$-heteroaryl-$C_2$–$C_{18}$-alkenyl, $C_1$–$C_{18}$-alkoxy-$C_1$–$C_{18}$-alkyl, $C_1$–$C_{18}$-alkoxy-$C_2$–$C_{18}$-alkenyl, $C_6$–$C_{18}$-aryloxy-$C_1$–$C_{18}$-alkyl, $C_6$–$C_{18}$-aryloxy-$C_2$–$C_{18}$-alkenyl, $C_3$–$C_8$-cycloalkyl, $C_3$–$C_8$-cycloalkyl-$C_1$–$C_{18}$-alkyl, $C_3$–$C_8$-cycloalkyl-$C_2$–$C_{18}$-alkenyl, and $CR^8R^9$—$O_n$—$(CO)_m$—$R^{10}$ and the radicals $R^3$ and $R^4$ are selected independently of one another from the group consisting of H, substituted or unsubstituted $C_1$–$C_{18}$-aryl, $C_3$–$C_{18}$-heteroaryl, $C_1$–$C_{18}$-alkyl, $C_2$–$C_{18}$-alkenyl, $C_2$–$C_{18}$-alkynyl, $C_6$–$C_{18}$-aryl-$C_1$–$C_{18}$-alkyl, $C_3$–$C_{18}$-heteroaryl-$C_2$–$C_{18}$-alkyl, $C_6$–$C_{18}$-aryl-$C_2$–$C_{18}$-alkenyl, $C_3$–$C_{18}$-heteroaryl-$C_2$–$C_{18}$-alkenyl, $C_1$–$C_{18}$-alkoxy-$C_1$–$C_{18}$-alkyl, $C_1$–$C_{18}$-alkoxy-$C_2$–$C_{18}$-alkenyl, $C_6$–$C_{18}$-aryloxy-$C_1$–$C_{18}$-alkyl, $C_6$–$C_{18}$-aryloxy-$C_2$–$C_{18}$-alkenyl, $C_3$–$C_{18}$-cycloalkyl, $C_3$–$C_8$-cycloalkyl-$C_1$–$C_{18}$-alkyl, and $C_3$–$C_8$-cycloalkyl-$C_2$–$C_{18}$-alkenyl or the radicals $R^3$ and $R^4$ form, together with the carbon to which they are bonded, an unsubstituted or substituted or a heteroatom-containing cycloalkylidene and Nu is $OR^5$, $SR^5$ or $NR^6R^7$, where the radicals $R^5$ are selected from the group consisting of H, substituted or unsubstituted $C_1$–$C_{18}$-alkyl, $C_2$–$C_{18}$-alkenyl, $C_2$–$C_{18}$-alkynyl, $C_6$–$C_{18}$-aryl-$C_1$–$C_{18}$-alkyl, $C_3$–$C_{18}$- heteroaryl-$C_1$–$C_{18}$-alkyl, $C_6$–$C_{18}$-aryl-$C_2$–$C_{18}$-alkenyl, and $C_3$–$C_{18}$-heteroaryl-$C_1$–$C_{18}$-alkenyl, and the radicals $R^6$ and $R^7$ are selected independently of one another from the group consisting of H, substituted or unsubstituted $C_1$–$C_{16}$-alkyl, $C_2$–$C_{18}$-alkenyl, $C_2$–$C_{18}$-alkynyl, $C_6$–$C_{18}$-aryl, $C_3$–$C_{18}$-heteroaryl, $C_6$–$C_{18}$-aryl-$C_1$–$C_{18}$-alkyl, $C_3$–$C_{18}$-heteroaryl-$C_1$–$C_{18}$-alkyl, $C_6$–$C_{18}$-aryl-$C_2$–$C_{18}$-alkenyl, and $C_3$–$C_{16}$-heteroaryl-$C_2$–$C_{18}$-alkenyl and the radicals $R^8$ and $R^9$ are selected independently of one another from the group consisting of substituted or unsubstituted $C_6$–$C_{18}$-aryl, $C_3$–$C_{18}$-heteroaryl, $C_1$–$C_{18}$-alkyl, $C_2$–$C_{18}$-alkenyl, $C_2$–$C_{18}$-alkynyl, $C_6$–$C_{18}$-aryl-$C_1$–$C_{18}$-alkyl, $C_3$–$C_{18}$-heteroaryl-$C_1$–$C_{18}$-alkyl, $C_6$–$C_{18}$-aryl-$C_2$–$C_{18}$-alkenyl, $C_3$–$C_{18}$-heteroaryl-$C_2$–$C_{18}$-alkenyl, $C_1$–$C_{18}$-alkoxy-$C_1$–$C_{18}$-alkyl, $C_1$–$C_{18}$-alkoxy-$C_2$–$C_{18}$-alkenyl, $C_6$–$C_{18}$-aryloxy-$C_1$–$C_{18}$-alkyl, $C_6$–$C_{18}$-aryloxy-$C_2$–$C_{18}$-alkenyl, $C_1$–$C_8$-cycloalkyl, $C_3$–$C_8$-cycloalkyl-$C_1$–$C_{18}$-alkyl, and $C_3$–$C_{18}$-cycloalkyl-$C_2$–$C_{18}$-alkenyl or the radicals $R^8$ and $R^9$ form, together with the carbon to which they are bonded, an unsubstituted or substituted or a heteroatom-containing cycloalkylidene, and m and n are, independently of one another, 0 or 1, and the following applies to the radical $R^{10}$: if m is 0 then the radical $R^{10}$ is selected from the group consisting of substituted or unsubstituted $C_1$–$C_{18}$-alkyl, $C_2$–$C_{18}$-alkenyl or $C_2$–$C_{18}$-alkynyl, substituted or unsubstituted $C_6$–$C_{18}$-aryl, $C_3$–$C_{18}$-heteroaryl, and substituted or unsubstituted silaalkyl or silaaryl, and if m is 1 then the radical $R^{10}$ is selected from the group consisting of substituted or unsubstituted aryl, substituted or unsubstituted $C_1$–$C_{18}$-alkyl, $C_2$–$C_{18}$-alkenyl or $C_2$–$C_{18}$-alkynyl.

Where the radicals are substituted radicals, these are preferably substituted by alkyl, alkenyl, alkynyl, aryl, heteroaryl, hydroxyl, alkoxy, carboxylate, alkoxycarbonyl, amino, nitro or halo radicals.

Where the abovementioned radicals contain a heteroatom, it is preferably O, N or S.

Mixtures of enantiomers of the general formula (I)

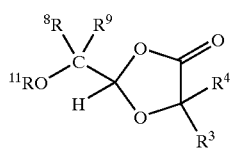

(I)

where $R^3$, $R^4$, $R^8$ and $R^9$ have the meaning mentioned above, and $R^{11}$ are substituted or unsubstituted, branched or unbranched $C_1$–$C_{18}$-alkyl, $C_2$–$C_{18}$-alkenyl or $C_2$–$C_{18}$-alkynyl, substituted or unsubstituted aryl, substituted or unsubstituted silaalkyl or silaaryl, or $R^{11}$ is $COR^{10}$ where $R^{10}$ has the meaning mentioned above, are preferably used.

Mixtures of enantiomers of the general formula (II)

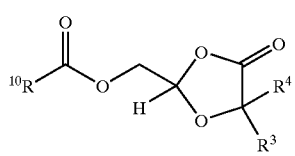

(II)

where $R^3$ and $R^4$ have the meaning mentioned above, and $R^{10}$ is selected from the group consisting of substituted or unsubstituted aryl, substituted or unsubstituted $C_1$–$C_{18}$-alkyl, $C_2$–$C_{18}$-alkenyl and $C_2$–$C_{18}$-alkynyl, are particularly preferably used.

The nucleophile NuH is preferably an oxygen-containing nucleophile $OR^5$.

The oxygen-containing nucleophile is particularly preferably a lower, unbranched alcohol, (e.g. methanol ($R^5$=$CH_3$) or ethanol ($R^5$=$CH_2CH_3$)) or water ($R^5$=H).

All enzymes able to cleave an ester linkage are in principle suitable for the process of the invention. Preference is given to a lipase or esterase of class 3.1 of the international enzyme nomenclature, Committee of the International Union of Biochemistry and Molecular Biology. Because they are easy to obtain, particular preference is given to lipases or esterases of microbial origin, pig pancreatic lipase, horse liver esterase or pig liver esterase.

Examples of enzymes of microbial origin which may be mentioned are enzymes from fungi, yeasts or bacteria such as, for example, *Alcaligenes* sp., *Aspergillus niger*, *Aspergillus oryzae*, *Bacillus* sp., *Bacillus stearothermophilus*, *Bacillus thermoglucosidasius*, *Candida antarctica*, *Candida lipolytica*, *Candida rugosa*, *Chromobacterium viscosum*, *Geotrichium candium*, *Mucor miehei*, *Penicillium camembertii*, *Penicillium roquefortii*, *Pseudomonas cepacia*, *Pseudomonas fluorescens*, *Pseudomonas* sp., *Rhizomucor javanicus*, *Rhizopus arrhizus*, *Rhizopus niveus*, *Saccharomyces cerevisae*, *Thermoanaerobium brockii*, *Thermomyces lanuginosa*. Particular preference is moreover given to lipases and esterases from *Candida* species such as, for example, *Candida antarctica* B.

Very particular preference is given to NOVOZYM® 435, 525 (commercially available from Novo, Denmark), CHIRAZYM® L2, E1, E2 and L7 (commercially available from Boehringer Mannheim, Germany) as enzyme. NOVOZYM® is a trademark for a product, the active ingredient of which is a lipase of *Candida antarctica* B. CHIRAZYM® is a trademark for a product, in which the active ingredient is as follows:

L2 is for Lipase from *Candida antarctica* B;
E1 is for Esterase from pig liver;
E2 is for Esterase from pig liver; and
L7 is for Lipase from porcine pancreas.

The enzyme is employed in the reaction directly or in immobilized form bound to a wide variety of carriers.

An immobilized form can be prepared in a manner known per se. This is possible, for example, by the enzyme being dissolved in a buffer at a suitable pH and then being passively absorbed onto the carrier such as, for example, diatomaceous earth (CELITE®, activated carbon, alumina, silica gel, kieselguhr, monodisperse soluble organosiloxane particles or resins (e.g. AMBERLITE®, DOWEX®). An alternative possibility is for the enzymes also to be covalently bonded to the carrier (e.g. polystyrene or epoxy resins such as EUPERGIT®). An enzyme which has been bound to a carrier in this way, for example, can be dried by lyophilization.

The amount of enzyme to be employed in the process of the invention depends on the nature of the precursor and of the product and on the activity of the enzyme preparation. The amount of enzyme which is optimal for the reaction can be established by simple preliminary tests.

Depending on the enzyme, the enzyme/substrate ratio, calculated as molar ratio between enzyme and dioxolanone/oxathiolanone derivative, is usually between 1:1,000 and 1:50,000,000 or more, preferably from 1:10,000 to 1:5,000,000.

The process of the invention can be carried out both in pure nucleophile (NuH) as solvent and in mixtures of the nucleophile (NuH) with aprotic or protogenic solvents or mixtures of solvents as long as these do not affect the reactivity of the enzyme with hydrolytic activity or lead to unwanted side reactions.

The reaction is advantageously carried out in a mixture of the nucleophile and a suitable solvent. Examples of suitable solvents are aliphatic or aromatic hydrocarbons such as hexane, cyclohexane, petroleum ether or toluene, halogenated hydrocarbons such as methylene chloride or chloroform, ethers such as methyl tert-butyl ether (MTBE), diethyl ether, diisopropyl ether, THF or dioxane, esters, acetonitrile or, where appropriate, alcohols which do not represent a nucleophile in relation to the above-mentioned enzymatic reaction, such as, for example, tertiary alcohols, or mixtures of said compounds.

The nucleophile/solvent ratio (v/v) is in this case preferably in a range from 1:10,000 to 1,000:1.

Mixtures of the nucleophile with aprotic solvents such as MTBE or diisopropyl ether in a nucleophile/solvent ratio (v/v) of from 1:100 to 100:1 are particularly preferred.

If water is used as nucleophile (Nu=OH), it is possible for maintenance of a preset pH to adjust the latter by adding a buffer. An $Na_2HPO_4/NaH_2PO_4$ buffer with a pH of 7.0 is preferably used for this purpose. It is also possible for the same purpose to meter in an aqueous alkali, preferably a solution of an alkali metal hydroxide in water, particularly preferably an aqueous solution of NaOH or KOH.

The reaction is advantageously carried out at a temperature between 0° C. and 75° C., preferably between 10° C. and 60° C., particularly preferably between 20° C. and 50° C.

The reaction times depend on the substitution pattern of the dioxolanone, choice of the nucleophile and solvent and the nature and amount of the enzyme and are between 10 minutes and 7 days. The reaction times are preferably between 1 and 48 hours.

The progress of the reaction can easily be followed by conventional methods, for example by HPLC. The progress of the reaction can preferably be determined by measuring the change in the optical rotation of the reaction solution in a polarimeter. The progress of the reaction is particularly preferably determined on line by measuring the optical rotation in a subsidiary circuit of the reactor. The termination of the reaction can depend on the desired result (high conversion, high enantiomeric excess of the substrate). In the ideal case, the reaction is terminated when the conversion is 50% with a high enantiopurity in the substrate.

The reaction is preferably terminated for example by separating the substrate or the product from the enzyme, for example by extraction of the aqueous phase or filtration. The reaction can also be stopped by inactivating the enzyme, for example by thermal or chemical denaturation.

If the reaction is carried out by repeated, continuous pumping of the reaction solution through a container packed with enzyme (a particularly preferred procedure), the reaction is preferably terminated by terminating the pumping.

The uncleaved, pure enantiomer is preferably isolated by removing the byproducts of the reaction and the solvent.

The free carbonyl compound $R^1COR^2$ resulting from the cleavage of a 1,3-dioxolan-4-one or 1,3-oxathiolan-5-one ring and the acid derivative $HXCR^3R^4CONu$ can be removed from the reaction solution by simple physical operations. This preferably takes place by distillation.

It is additionally possible for further breakdown products formed on cleavage of other functional groups in the molecule to be removed easily. This preferably takes place by distillation.

It is preferred for the low-boiling compounds to be removed first by distillation. It has been found, surprisingly, that the alcohol ($R^1$=H, $R^-$=$CH_2OH$) which is a byproduct of the racemate resolution of an ester dioxolanone (X=O; $R^1$=H, $R^2$=$CH_2$—O—(CO)—$R^{10}$) can be removed by simple extraction, preferably with water.

The carbonyl compound resulting from the enzymatic reaction is an important, costly precursor for the synthesis of racemic 1,3-dioxolan-4-one and 1,3-oxathiolan-5-one compounds. It is preferably employed, in order to save chemicals and costs, in the synthesis of 1,3-dioxolan-4-ones and 1,3-oxathiolan-5-ones (see scheme 1).

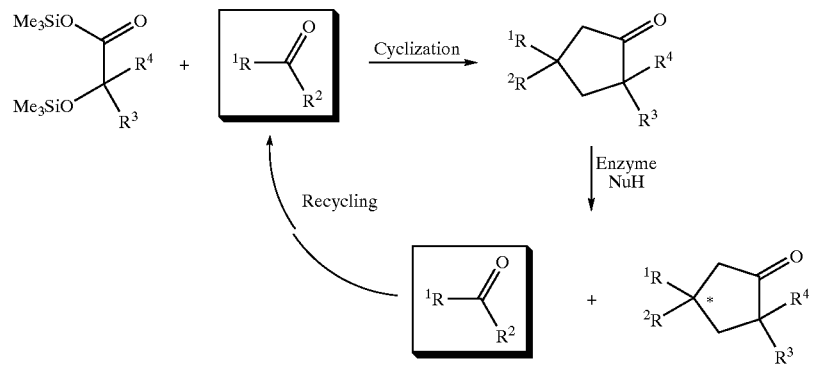

Scheme 1: Recycling of the carbonyl compound resulting from the racemate resolution for the example of 1,3-dioxolan-4-ones.

DETAILED DESCRIPTION OF PREFERRED EMBODIMENTS

Other objects and features of the present invention will become apparent from the following detailed description considered in connection with the accompanying examples. It is to be understood, however, that the examples are designed as an illustration only and not as a definition of the limits of the invention.

EXAMPLE 1

(4-oxo-1,3-dioxolan-2-yl)methyl (+)-(R)-2-methylpropanoate (Batch Process)

50.0 g (0.27 mol) of racemic (4-oxo-1,3-dioxolan-2-yl) methyl 2-methylpropanoate (X=O; $R^1$=H; $R^2$=$CH_2$—O—(CO)—CH($CH_3$)$_2$; $R^3$, $R^4$=H) are dissolved in a mixture of 185 ml of MTBE and 185 ml of methanol (Nu=$OCH_3$) in a 114-necked flask. 2.6 g of NOVOZYM® 435 are added to this solution, and the mixture is stirred vigorously.

A polarimeter is connected via a bypass system to the 4-necked flask and is used to follow the progress of the reaction through measurement of the optical rotation of the solution. When the desired enantiopurity (reaction followed by chiral GC) is reached, the reaction is terminated by filtering the reaction mixture to remove undissolved enzymes. The reaction mixture is then concentrated in vacuo. The residue is then taken up in 100 ml of MTBE and washed twice with 100 ml of water each time. The organic phase is dried over $Na_2SO_4$ and then freed of solvent in vacuo. The crude product is purified by distillation.

Yield: 10.3 g (0.05 mol; 20%)
Boiling point: 55° C. (0.02 mbar)
$[\alpha]_D^{20}$=+19.8 (neat); ee>98%.

EXAMPLE 2

(4-Oxo-1,3-dioxolan-2-yl)methyl (+)-(R)-2-methylpropanoate (Column Process)

50.0 g (0.27 mol) of racemic (4-oxo-1,3-dioxolan-2-yl) methyl 2-methylpropanoate (X=O; $R^1$=H; $R^2$=$CH_2$—O—(CO)—CH($CH_3$)$_2$; $R^3$, $R^4$=H) are dissolved in a mixture of 185 ml of MTBE and 185 ml of methanol (Nu=$OCH_3$) in a thermostated 0.61 glass flask. A separate glass column is packed with 1.3 g of NOVOZYM® 435, and the substrate/solvent mixture is pumped via a tubing system through the glass column (flow rate 600 ml/h). The reaction is stopped (after ~25 h) by terminating the pumping, and the crude product is purified as described in example 1.

EXAMPLES 3–8

The following examples were carried out in accordance with the method of example 1.

| | Substituents in equation 5 | Racemate | Product | Selectivity according t Sih* |
|---|---|---|---|---|
| 3 | X = O; $R^1$ = H; $R^2$ = —$CH_2$—$C_6H_5$; $R^3$, $R^4$ = H | | (+)-2-Methylphenyl-1,3-dioxolan-4-one | 11 |
| 4 | X = O; $R^1$ = H; $R^2$ = —$C_6H_{11}$; $R^3$, $R^4$ = H | | (+)-2-Cyclohexyl-1,3-dioxolan-4-one | 65 |
| 5 | X = O; $R^1$ = H; $R^2$ = —CH($CH_3$)$_2$; $R^3$, $R^4$ = H | | (+)-2-iso-Propyl-1,3-dioxolan-4-one | 14 |
| 6 | X = O; $R^1$ = H; $R^2$ = —$C_7H_{15}$; $R^3$, $R^4$ = H | | (+)-2-Heptyl-1,3-dioxolan-4-one | 13 |
| 7 | X = S; $R^1$ = H; $R^2$ = —$C_6H_{11}$; $R^3$, $R^4$ = H | | (+)-2-Cyclohexyl-1,3-oxathiolan-5-one | 65 |
| 8 | X = S; $R^1$ = H; $R^2$ = —$CH_2$O(CO)—CH($CH_3$)$_2$; $R^3$, $R^4$ = H | | (+)-Isobutyryloxymethyl-1,3-oxathiolan-5-one | 65 |

*Chen, C.-S. et al., J. Am. Chem. Soc. 104, 7294–7299 (1982)

Accordingly, while only several embodiments of the present invention have been shown and described, it is obvious that many changes and modifications may be made thereunto without departing from the spirit and scope of the invention.

What is claimed is:

1. A process for preparing an enantiopure substituted 1,3-dioxolan-4-one or an enantiopure substituted 1,3-oxathiolan-5-one which comprises bringing a mixture containing a substance selected from the group consisting of a recemic 1,3-dioxolan-4-one and a racemic 1,3-oxathiolan-5-one and an enzyme with hydrolytic activity into contact with an effective amount of a nucleophile to effect the biotransformation; cleaving the dioxolane or oxathiolane ring of one enantiomer selected from the group consisting of the 1,3-dioxolan-4-one ring and the 1,3-oxathiolan-5-one ring by the enzyme with hydrolytic activity; and after the cleaving of one enantiomer has taken place, isolating the uncleaved enantiomer selected from the group consisting of the 1,3-dioxolan-4-one and 1,3-oxathiolane-5-one.

2. The process as claimed in claim 1, wherein a mixture containing a substance selected from the group consisting of the racemic substituted 1,3-dioxolan-4-one and the racemic substituted 1,3-oxathiolan-5-one is cleaved by means of an enzyme which is able to cleave an ester linkage in the presence of a nucleophile (NuH) as depicted in the equation,

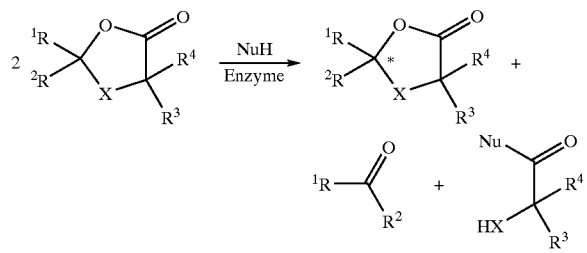

where X=oxygen or sulfur and the radicals $R^1$ and $R^2$ are different and are selected independently of one another from the group consisting of H, substituted or unsubstituted $C_6$–$C_{18}$-aryl, substituted or unsubstituted $C_3$–$C_{18}$-heteroaryl, substituted or unsubstituted $C_1$–$C_{18}$-alkyl, substituted or unsubstituted $C_2$–$C_{18}$-alkenyl, substituted or unsubstituted $C_2$–$C_{18}$-alkynyl, substituted or unsubstituted $C_6$–$C_{18}$-aryl-$C_1$–$C_{18}$-alkyl, substituted or unsubstituted $C_3$–$C_{18}$-heteroaryl-$C_1$–$C_{18}$-alkyl, substituted or unsubstituted $C_6$–$C_{18}$-aryl-$C_2$–$C_{18}$-alkenyl, substituted or unsubstituted $C_3$–$C_{18}$-heteroaryl-$C_2$–$C_{18}$-alkenyl, substituted or unsubstituted $C_1$–$C_{18}$-alkoxy-$C_1$–$C_{18}$-alkyl, substituted or unsubstituted $C_1$–$C_{18}$-alkoxy-$C_2$–$C_{18}$-alkenyl, substituted or unsubstituted $C_6$–$C_{18}$-aryloxy-$C_1$–$C_{18}$-alkyl, substituted or unsubstituted $C_6$–$C_{18}$-aryloxy-$C_2$–$C_{18}$-alkenyl, substituted or unsubstituted $C_3$–$C_8$-cycloalkyl, substituted or unsubstituted $C_3$–$C_8$-cycloalkyl-$C_1$–$C_{18}$-alkyl, substituted or unsubstituted $C_3$–$C_8$-cycloalkyl-$C_2$–$C_{18}$-alkenyl, and substituted or unsubstituted $CR^8R^9$—$O_n$—$(CO)_m$—$R^{10}$ and the radicals $R^3$ and $R^4$ are selected independently of one another from the group consisting of H, substituted or unsubstituted $C_6$–$C_{18}$-aryl, substituted or unsubstituted $C_3$–$C_{18}$-heteroaryl, substituted or unsubstituted $C_1$–$C_{18}$-alkyl, substituted or unsubstituted $C_2$–$C_{18}$-alkenyl, substituted or unsubstituted $C_2$–$C_{18}$-alkynyl, substituted or unsubstituted $C_6$–$C_{18}$-aryl-$C_1$–$C_{18}$-alkyl, substituted or unsubstituted $C_3$–$C_{18}$-heteroaryl-$C_1$–$C_{18}$-alkyl, substituted or unsubstituted $C_6$–$C_{18}$-aryl-$C_2$–$C_{18}$-alkenyl, substituted or unsubstituted $C_3$–$C_{18}$-heteroaryl-$C_2$–$C_{18}$-alkenyl, substituted or unsubstituted $C_1$–$C_{18}$-alkoxy-$C_1$–$C_{18}$-alkyl, substituted or unsubstituted $C_1$–$C_{18}$-alkoxy-$C_2$–$C_{18}$-alkenyl, substituted or unsubstituted $C_6$–$C_{18}$-aryloxy-$C_1$–$C_{18}$-alkyl, substituted or unsubstituted $C_6$–$C_{18}$-aryloxy-$C_2$–$C_{18}$-alkenyl, substituted or unsubstituted $C_3$–$C_{18}$-cycloalky, substituted or unsubstituted $C_3$–$C_8$-cycloalkyl-$C_1$–$C_{18}$-alkyl, and substituted or unsubstituted $C_3$–$C_{18}$-cycloalkyl-$C_2$–$C_{18}$-alkenyl or the radicals $R^3$ and $R^4$ form, together with the carbon to which they are bonded, an unsubstituted or substituted or a heteroatom-containing cycloalkylidene and Nu is $OR^5$, $SR^5$ or $NR^6R^7$, where the radical $R^5$ is selected from the group consisting of H, substituted or unsubstituted $C_1$–$C_{18}$-alkyl, substituted or unsubstituted $C_2$–$C_{18}$-alkenyl, substituted or unsubstituted $C_2$–$C_{18}$-alkynyl, substituted or unsubstituted $C_6$–$C_{18}$-aryl-$C_1$–$C_{18}$-alkyl, substituted or unsubstituted $C_3$–$C_{18}$-heteroaryl-$C_1$–$C_{18}$-alkyl, substituted or unsubstituted $C_6$–$C_{18}$-aryl-$C_2$–$C_{18}$-alkenyl, substituted or unsubstituted $C_3$–$C_{18}$-heteroaryl-$C_2$–$C_{18}$-alkenyl, and the radicals $R^6$ and $R^7$ are selected independently of one another from the group consisting of H, substituted or unsubstituted $C_1$–$C_{18}$-alkyl, substituted or unsubstituted $C_2$–$C_{18}$-alkenyl, substituted or unsubstituted $C_2$–$C_{18}$-alkynyl, substituted or unsubstituted $C_6$–$C_{18}$-aryl, substituted or unsubstituted $C_3$–$C_{18}$-heteroaryl, substituted or unsubstituted $C_6$–$C_{18}$-aryl-$C_1$–$C_{18}$-alkyl, substituted or unsubstituted $C_3$–$C_{18}$-heteroaryl-$C_1$–$C_{18}$-alkyl, substituted or unsubstituted $C_6$–$C_{18}$-aryl-$C_2$–$C_{18}$-alkenyl, and substituted or unsubstituted $C_3$–$C_{18}$-heteroaryl-$C_2$–$C_{18}$-alkenyl and the radicals $R^8$ and $R^9$ are selected independently of one another from the group consisting of substituted or unsubstituted $C_6$–$C_{18}$-aryl, substituted or unsubstituted $C_3$–$C_{18}$-heteroaryl, substituted or unsubstituted $C_1$–$C_{18}$-alkyl, substituted or unsubstituted $C_2$–$C_{18}$-alkenyl, substituted or unsubstituted $C_2$–$C_{18}$-alkynyl, substituted or unsubstituted $C_6$–$C_{18}$-aryl-$C_1$–$C_{18}$-alkyl, substituted or unsubstituted $C_3$–$C_{18}$-heteroaryl-$C_1$–$C_{18}$-alkyl, substituted or unsubstituted $C_6$–$C_{18}$-aryl-$C_2$–$C_{18}$-alkenyl, substituted or unsubstituted $C_3$–$C_{18}$-heteroaryl-$C_2$–$C_{18}$-alkenyl, substituted or unsubstituted $C_1$–$C_{18}$-alkoxy-$C_1$–$C_{18}$-alkyl, substituted or unsubstituted $C_1$–$C_{18}$-alkoxy-$C_2$–$C_{18}$-alkenyl, substituted or unsubstituted $C_6$–$C_{18}$-aryloxy-$C_1$–$C_{18}$-alkyl, substituted or unsubstituted $C_6$–$C_{18}$-aryloxy-$C_2$–$C_{18}$-alkenyl, substituted or unsubstituted $C_3$–$C_{18}$-cycloalkyl, substituted or unsubstituted $C_3$–$C_{18}$-cycloalkyl-$C_1$–$C_{18}$-alkyl, and substituted or unsubstituted $C_3$–$C_{18}$-cycloalkyl-$C_2$–$C_{18}$-alkenyl or the radicals $R^8$ and $R^9$ form, together with the carbon to which they are bonded, an unsubstituted or substituted or a heteroatom-containing cycloalkylidene, and m and n are, independently of one another, 0 or 1, and the following applies to the radical $R^{10}$:

if m is 0 then the radical $R^{10}$ is selected from the group consisting of substituted or unsubstituted $C_1$–$C_{18}$-alkyl, substituted or unsubstituted $C_2$–$C_{18}$-alkenyl and substituted or unsubstituted $C_2$–$C_{18}$-alkynyl, substituted or unsubstituted $C_6$–$C_{18}$-aryl, substituted or unsubstituted $C_3$–$C_{18}$-heteroaryl, substituted or unsubstituted silaalkyl and substituted or unsubstituted silaaryl, and if m is 1 then the radical $R^{10}$ is selected from the group consisting of substituted or unsubstituted aryl, substituted or unsubstituted $C_1$–$C_{18}$-alkyl, substituted or unsubstituted $C_2$–$C_{18}$-alkenyl and substituted or unsubstituted $C_2$–$C_{18}$-alkynyl; and said each substituted radical is substituted by a group selected from the group consisting of alkyl, alkenyl, alkynl, aryl, heteroaryl, hydroxyl, alkoxy, carboxylate, alkoxycarbonyl, amino, nitro, and halo; and wherein if said radical contain a heteroatom, it is selected from the group consisting of O, N, and S.

3. The process as claimed in claim 1, wherein the enzyme with hydrolytic activity is selected from the group consisting of a lipase and an esterase.

4. The process as claimed in claim 1, wherein the enzyme is employed in a manner selected from the group consisting of in solution form and in immobilized form.

5. The process as claimed in claim 1, wherein the enzyme to dioxolanone or oxathiolanone ratio, calculated as molar ratio between enzyme and dioxolanone or oxathiolanone, is from 1:1,000 to 1:50,000,000.

6. The process as claimed in claim 1, wherein the nucleophile is an oxygen-containing nucleophile.

7. The process as claimed in claim 6, wherein the oxygen-containing nucleophile is selected from the group consisting of a lower unbranched alcohol and water.

8. The process as claimed in claim 7, wherein the lower unbranched alcohol is selected from the group consisting of methanol and ethanol.

9. The process as claimed in claim 1, which is carried out in the presence of a solvent.

10. The process as claimed in claim 9, wherein the solvent is selected from the group consisting of aliphatic hydrocarbons, aromatic hydrocarbons, halogenated hydrocarbons, ethers, alcohols, esters, acetonitrile and mixtures thereof.

11. The process as claimed in claim 1, wherein the reaction is carried out at temperatures between 0 and 75° C.

12. The process as claimed in claim 1, wherein the reaction is carried out for between 10 minutes and 7 days.

13. The process as claimed in claim 1, wherein the uncleaved enantiomer is isolated by removing byproducts of the reaction.

14. The process as claimed in claim 13, wherein the byproducts are removed by a manner selected from the group consisting of extraction and distillation.

* * * * *